(12) United States Patent
Piramal et al.

(10) Patent No.: US 10,098,869 B2
(45) Date of Patent: Oct. 16, 2018

(54) COMPOUNDS FOR THE TREATMENT OF CANCERS ASSOCIATED WITH HUMAN PAPILLOMAVIRUS

(71) Applicant: Piramal Enterprises Limited, Mumbai (IN)

(72) Inventors: Swati Ajay Piramal, Mumbai (IN); Muralidhara Padigaru, Mumbai (IN); Veena R. Agarwal, Mumbai (IN); Gandhali Ashwin Deshpande, Mumbai (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 15/231,684

(22) Filed: Aug. 8, 2016

(65) Prior Publication Data

US 2017/0189378 A1    Jul. 6, 2017

Related U.S. Application Data

(63) Continuation of application No. 14/127,675, filed as application No. PCT/IB2012/053166 on Jun. 22, 2012, now abandoned.

(Continued)

(51) Int. Cl.
*A61K 31/40* (2006.01)
*A61K 31/4025* (2006.01)
(Continued)

(52) U.S. Cl.
CPC .......... *A61K 31/4025* (2013.01); *A61K 45/06* (2013.01); *C07D 405/04* (2013.01)

(58) Field of Classification Search
CPC .................................................. A61K 31/4025
(Continued)

(56) References Cited

U.S. PATENT DOCUMENTS

| 8,895,605 | B2* | 11/2014 | Rathos | A61K 31/00 |
|---|---|---|---|---|
| | | | | 514/422 |
| 2007/0015802 | A1* | 1/2007 | Lal | C07D 405/14 |
| | | | | 514/365 |
| 2010/0152129 | A1* | 6/2010 | Giridharan | A61K 31/7068 |
| | | | | 514/49 |

FOREIGN PATENT DOCUMENTS

| WO | 2008139271 A2 | 11/2008 |
|---|---|---|
| WO | 2010128443 A1 | 11/2010 |
| WO | WO2010/128443 | * 11/2010 |

OTHER PUBLICATIONS

Kalpana S. Joshi et al., In Vitro Antitumor Propoerties of a Novel Cyclin-Dependent Kinase Inhibitor P276-00, Molecular Cancer Therapeutics, American Association of Cancer Research, vol. 6, No. 3, pp. 918-925 (2007) XP002503867, ISSN: 1535-7163 DOI: 10.115811535-7163 MCT-06-0613 Abstract Figure 1—Table 2.

(Continued)

*Primary Examiner* — Shengjun Wang
(74) *Attorney, Agent, or Firm* — Morgan, Lewis & Bockius LLP

(57) ABSTRACT

The present invention relates to the pyrrolidine substituted with flavone derivatives, represented by the compounds of Formula (I) or a pharmaceutically acceptable salt, a solvate, a stereoisomer or a diastereoisomer thereof for use in the treatment of cancers associated with human papillomavirus. The present invention also relates to the pharmaceutical compositions containing the compounds of Formula (I) for the treatment of cancers associated with human papillomavirus.

11 Claims, 4 Drawing Sheets

Specification includes a Sequence Listing.

Related U.S. Application Data (60) Provisional application No. 61/500,799, filed on Jun. 24, 2011.

(51) Int. Cl.
*A61K 45/06* (2006.01)
*C07D 405/04* (2006.01)

(58) Field of Classification Search
USPC .......................................................... 514/422
See application file for complete search history.

(56) References Cited

OTHER PUBLICATIONS

Cho Nam Hoon et al., "Alteration of Cell Cycle in Cervical Tumor Associated with Human Papillomavirus: Cyclin-Dependent Kinase Inhibitors", Yonsei Medical Journal, vol. 43, No. 6, pp. 722-728 (2002). XP002688903. ISSN: 0513-5796 Abstract.
Zehbe Ingeborg et al., "Overriding of Cyclin-Dependent Kinase Inhibitors by High and Low Risk Human Papillomavirus Types: Evidence for an in Vivo Role in Cervical Lesions", Oncogene, vol. 18, No. 13, pp. 2201-2211 (1999), XP002688904. ISSN: 0950-9232 Abstract.
Luczak M. W et al., "Apicidin Down-Regulates Human Papillomavirus Type 16 E6 and E7 Transcripts and Proteins in SiHa Cervical Cancer Cells", Cancer Letters, vol. 272, No. 1, pp. 53-60 (2008), XP025562827. ISSN: 0304-3835. DOI: 10.1016/J.Canlet.2008.06.030 [Retrieved on Aug. 6, 2008] Abstract p. 57, col. 2, Paragraph 1.
Michelle S. Longworth, et al., "Pathogenesis of Human Papillomaviruses in Differentiating Epithelia", Microbiology and Molecular Biology Reviews, vol. 68, No. 2, pp. 362-372 (2004).
Gypsyamber D'Souza, Ph.D., et al., "Case-Control Study of Human Papillomavirus and Oropharyngeal Cancer", The New England Journal of Medicine, vol. 356, No. 19, pp. 1944-1956 (2007).
Donald Maxwell Parkin, "The Global Health Burden of Infection Associated Cancers in the Year 2002", Int. J. Cancer, vol. 118, No. 12, pp. 3030-3044 (2006).
Aimee R. Kreimer et al., "Human Papillomavirus Types in Head and Neck Squamous Cell Carcinomas Worldwide: A Systematic Review", Cancer Epidemiology, Biomarkers and Prevention, vol. 14, No. 2, pp. 467-475 (2005).
Friederike Klein et al., "Incidence of Human Papilloma Virus in Lung Cancer", Lung Cancer, vol. 65, pp. 13-18 (2009).
Yan Yu et al., "Correlation of HPV-16/18 Infection of Human Papillomavirus with Lung Aquamous Cell Carcinomas in Western China", Oncology Reports, vol. 21, pp. 1627-1632 (2009).
Hugo De Vayst et al., "Prevalence and Type Distribution of Human Papillomavirus in Carcinoma and Intraepithelial Neoplasia of the Vulva, Vagina and Anus: A Meta-Analysis", International Journal of Cancer, vol. 124, No. 7, pp. 1626-1636 (2009).
Studies of Cancer in Humans, LARC Monographs, vol. 64, pp. 87-231 (1995).
Nicolai Christian Sjo et al., "Human Papillomavirus in Conjunctival Papilloma", Br. J. Ophthalmol., vol. 85, pp. 785-787 (2001).
Morten Frisch, M.D., Ph.D., et al., "Sexually Transmitted Infection as a Cause of Anal Cancer", The New England Journal of Medicine, vol. 337, No. 19, pp. 1350-1358 (1997).
Ahmedin Jemal, DVM, Ph.D., et al., "Cancer Statistics, 2010", A Cancer Journal for Clinicians, vol. 60, No. 5, pp. 277-300 (2010).
D. Maxwell Parkin et al., "The Burden of HPV-Related Cancers", Vaccine, vol. 24 (Supp. 3), pp. S11-S25 (2006).
Herbert Pfister, "Chapter 8: Human Papillomavirus and Skin Cancer", Journal of National Cancer Institute Monographs, No. 31, pp. 52-56 (2003).
Human Pappilomavirus and Related Cancers, Summary Report, Nov. 15, 2010.
Vijay A. Varma, M.D., et al., "Association of Human Papillomavirus with Penile Carcinoma: A Study Using Polymerase Chain Reaction and in Situ Hybridization", Hum. Pathol., vol. 22, pp. 908-913 (1991).
Jennifer S. Smith, Ph.D., MPH, et al., "Human Papillomavirus Type-Distribution in Vulvar and Vaginal Cancers and Their Associated Precursors", Obstetrics & Gynecology, vol. 113, No. 4, pp. 917-924 (2009).

* cited by examiner

FIG. 5

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agacttcgag caggagatg                                                    19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttgatcttc atggtgctag g                                                 21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaggtatat gactttgctt ttc                                               23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caagacatac atcgaccggt cc                                                22

<210> SEQ ID NO 5

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaatgacagc tcagaggagg ag                                              22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtttctgaga acagatgggg cac                                             23
```

COMPOUNDS FOR THE TREATMENT OF CANCERS ASSOCIATED WITH HUMAN PAPILLOMAVIRUS

CROSS-REFERENCE

This application is a continuation application of U.S. application Ser. No. 14/127,675 filed on Dec. 19, 2013, which is a 371 of International Application PCT/162012/053166, filed Jun. 22, 2012, which claims the benefit of U.S. Provisional Patent Application Ser. No. 61/500,799, filed Jun. 24, 2011, all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 16, 2017, is named 38029-735_301_SL.TXT and is 1.71 Kilobytes in size.

FIELD OF THE INVENTION

The present invention relates to the pyrrolidine substituted with flavone derivatives, represented by the compounds of Formula (I) (as described herein) or pharmaceutically acceptable salts, solvates, stereoisomers or diastereoisomers thereof for use in the treatment of cancers associated with human papillomavirus (HPV). The present invention also relates to pharmaceutical compositions containing the compounds of Formula (I) for use in the treatment of cancers associated with human papillomavirus.

BACKGROUND OF THE INVENTION

Human papillomavirus (HPV) is a circular, non-enveloped dsDNA virus that infects squamous epithelial cells. HPV enters the body, usually through a break in the skin, and then infects the cells in the layers of the skin. HPV is transmitted by skin-to-skin contact. HPV infections can be acquired through a cut or through sexual activity with an infected person. This includes kissing or touching the skin of the infected areas and having intercourse. A mother with a genital HPV infection may also transmit the virus to the infant during labour.

HPVs are a group of more than 120 related viruses, 33% of which are known to infect genital tract (*Microbiology and Molecular Biology Reviews*, 2004, 68 (2):362-372). Certain types of human papillomavirus are able to transform normal cells into abnormal ones which can go on to form cancer. Accordingly, these viruses are classified as high-risk types and low-risk types. High-risk HPVs are associated with cancers. Genital HPV infections are very common and can lead to anogenital cancers. Persistent infections with high-risk HPVs are the primary cause of cervical cancer. HPV infections also cause anal cancer, vulvar cancer, vaginal cancer and penile cancer (*Int. J. Cancer,* 2006, 118(12): 3030-44). The high risk subtypes are HPV 16, 18, 31, 33, 35, 39, 45, 51, 52, 56, 58, 59, 66 and 68, the most common being HPV 16, 18, 31, 33 and 45. Further, several types of HPVs, particularly type 16, have been found to be associated with HPV-positive oropharyngeal cancer, a form of head and neck cancer (*N. Engl. J. Med.,* 2007, 356(19):1944-56).

High risk HPVs produce two oncoproteins, E6 and E7, which are necessary for viral replication. During the HPV infection in humans, the HPV E6 protein binds and promotes the degradation of tumor suppressor p53 by an ubiquitin-mediated pathway diminishing the ability of the cell to undergo apoptosis. The HPV E7 protein binds and degrades the retinoblastoma protein (pRb), preventing it from inhibiting the transcription factor E2F, resulting in loss of cell cycle control.

It has been estimated that HPV accounts for approximately 5% of all cancers worldwide (*Int. J. Cancer,* 2006, 118(12):3030-3044).

Cancer of the cervix uteri is the second most common cancer among women worldwide. About 86% of the cases occur in developing countries. Cervical cancer accounts to 13% of the cancers occurring in females (World: Human Pappilomavirus and related cancers, summary report, November 2010).

Persistent Human papillomavirus (HPV) infections are now recognized as the cause of essentially all cervical cancers. According to the American Cancer Society, in 2010, about 12,000 women in the United States would be diagnosed with this type of cancer and more than 4,000 would die from it. Cervical cancer is diagnosed in nearly half a million women each year worldwide, claiming a quarter of a million lives annually.

Vulvar and Vaginal cancers account to about 3 to 5% and 1-2% respectively of all gynecologic cancers and penile cancers accounts to about 0.2% of all cancers in the United States. Despite their infrequency, vulvar, vaginal and penile cancers remain important diseases, because of their significant impact on sexuality. Though there is no single etiologic factor, there is a strong association with HPV infection. HPV is thought to be responsible for about 40% of penile cancers. Many studies have shown the presence of HPV types 16 and 18 in penile carcinoma (Hum. Pathol., 1991, 22:908-913). HPV is also responsible for about 65% of vaginal (*International Journal of Cancer,* 2009, 124(7):1626-1636) and 50% of vulvar cancers (*Vaccine,* 2006, 24(suppl 3): S11-S25) and HPV-16 accounted for most HPV positive cases for both the cancers (*Obstet. Gynecol.,* 2009, 113(4):917-24).

HPV infection is also associated with anal cancer. It is estimated that about 1,600 new cases of HPV-associated anal cancers are diagnosed in women and about 900 are diagnosed in men each year in the United States. In general, HPV is thought to be responsible for about 90% of anal cancers (*International Journal of Cancer,* 2009, 124(7): 1626-1636). Notably HPV 16 seems to be responsible for most of the anal cancer. According to a study HPV 16, was detected in 84 percent of anal cancer specimens examined (*New England Journal of Medicine,* 1997, 337(19):1350-8).

Cancer of head and neck typically refers to squamous cell carcinomas of the head and neck. Head and neck cancers account for approximately 3 percent of all cancers in the United States (*A Cancer Journal for Clinicians,* 2010, 60(5): 277-300). Head and neck cancers are identified by the area in which they begin. They are typically classified as: cancers of oral cavity, salivary gland, paranasal sinuses, nasal cavity, pharynx, nasopharynx, oropharynx, hypopharynx, larynx and lymph nodes in the upper part of the neck. Cancer of the oral cavity (the front two-thirds of the tongue, the gingiva, the buccal mucosa, the floor of the mouth under the tongue, the hard palate, and the small area behind the wisdom teeth) and cancer of the oropharynx (the soft palate, the base of the tongue, and the tonsils) are the most common types of cancer caused by HPV. Studies have shown that about 60% of oropharyngeal cancers are caused by HPV (*Cancer Epidemiology, Biomarkers and Prevention,* 2005, 14(2):467-475), in particular HPV16, is a causal factor for some head and neck squamous cell carcinoma (HNSCC).

HPV has also been associated with lung carcinomas. According to the published articles the incidence of HPV in lung cancer was 24.5% (*Lung Cancer*, 2009, 65: 13-18). A study conducted in China revealed that the risk of lung squamous cell carcinomas was 3.5 times higher among HPV-positive population compared with the HPV-negative population and 16.9 times higher for patients with positive HPV-16 than negative HPV-16 (*Oncol. Rep.*, 2009, 21(6): 1627-32).

A role for human papillomaviruses has also been proposed in a diverse range of other malignancies, particularly, non-melanoma skin cancer the commonest malignancy in fair-skinned populations worldwide. Skin cancer is rarely fatal and is responsible for less than 1% of all cancer deaths. However its impact on the public health is nevertheless considerable. The involvement of HPV in human skin cancer was first demonstrated in patients with the rare hereditary disease epidermodysplasia verruciformis (*Journal of National Cancer Institute Monographs*, 2003, No. 31).

HPV is also associated with intraepithelial neoplasia of the conjunctiva (0-80%) and in 62-100% of invasive carcinomas of the conjunctiva, eyelid and lacrimal sac (*IARC Monographs*, 64:130). There is a strong association between HPV and conjunctival papillomas. HPV type 6/11 is the most common HPV type in conjunctival papilloma (*Br. J. Ophthalmol.*, 2001, 85:785-787).

HPV 6, 11 and 13 are typically labeled as low-risk, because the infection with these types has low oncogenic potential and usually results in the formation of benign lesions such as genital warts (technically known as condylomata acuminata) and mild dysplasia of the cervix, HPV 6 and 11 are also associated with conjunctival papilloma.

Despite the high incidence of genital HPV infection and its association with malignant diseases, there is no effective antiviral therapy for HPV infection. Gardasil® and Cervarix® are the two vaccines currently on the market against two of the most common high risk HPVs (HPV 16 and 18). However, they are only of prophylactic type and do not treat the existing HPV associated cancer. Moreover, the high cost, issues with social acceptance, and limitations in health care systems through which the vaccine can be provided, limits the availability of this vaccine to women, particularly in developing countries where HPV-associated anogenital cancers (relating to the anus and the genitals) are most commonly found. Consequently there remains a need to identify other, less expensive and more universally available approaches for preventing and/or treating HPV associated cancers.

The inventors have surprisingly found that pyrrolidine substituted with flavone derivatives are effective against cancers associated with HPV.

The invention described herein provides pyrrolidine substituted with flavone derivatives represented by Formula (I) (as described herein) for the treatment of human papillomavirus associated cancers.

SUMMARY OF THE INVENTION

According to one aspect of the invention, there is provided use of a compound of Formula (I), a pharmaceutically acceptable salt, a solvate, a stereoisomer or a diastereoisomer thereof for the treatment of a cancer associated with human papillomavirus.

According to another aspect of the invention, there is provided use of a compound of Formula (I), a pharmaceutically acceptable salt, a solvate, a stereoisomer or a diastereoisomer thereof for the treatment of a cancer associated with HPV wherein the cancer is anal cancer, vulvar cancer, vaginal cancer, penile cancer, cervical cancer, head and neck cancer such as oropharyngeal cancer and cancer of the oral cavity, lung cancer, non-melanoma skin cancer or cancer of the conjunctiva.

According to yet another aspect of the invention, there is provided use of a compound of Formula (I), a pharmaceutically acceptable salt, a solvate, a stereoisomer or a diastereoisomer thereof for the treatment of cervical cancer.

According to another aspect of the invention, there is provided a method for the treatment of human papillomavirus associated cancers, comprising administering to the subject in need thereof a therapeutically effective amount of a compound of Formula (I) a pharmaceutically acceptable salt, a solvate, a stereoisomer or a diastereoisomer thereof.

According to another aspect of the invention, there is provided a method for the treatment of a cancer associated with HPV wherein the cancer is selected from anal cancer, vulvar cancer, vaginal cancer, penile cancer, cervical cancer, head and neck cancer such as oropharyngeal cancer and cancer of the oral cavity, lung cancer, non-melanoma skin cancer or cancer of the conjunctiva in a subject, comprising administering to the subject in need thereof a therapeutically effective amount of a compound of Formula (I), a pharmaceutically acceptable salt, a solvate, a stereoisomer or a diastereoisomer thereof.

According to yet another aspect of the invention, there is provided a method for the treatment of cervical cancer, comprising administering to the subject in need thereof a therapeutically effective amount of a compound of Formula (I), a pharmaceutically acceptable salt, a solvate, a stereoisomer or a diastereoisomer thereof.

According to another aspect of the invention there is provided a pharmaceutical composition, comprising a therapeutically effective amount of a compound of Formula (I) a pharmaceutically acceptable salt, a solvate, a stereoisomer or a diastereoisomer thereof in association with a pharmaceutically acceptable carrier for the treatment of a cancer associated with HPV.

According to another aspect of the invention, there is provided a method for the manufacture of medicaments, comprising a compound of Formula (I), a pharmaceutically acceptable salt, a solvate, a stereoisomer or a diastereoisomer thereof which are useful for the treatment of a cancer associated with HPV.

Other aspects and further scope of applicability of the present invention will become apparent from the detailed description to follow.

BRIEF DESCRIPTION OF THE DRAWINGS

FIG. 3 B is a graphical representation of p53-EGFP nuclear translocation in HeLa cells.

DETAILED DESCRIPTION OF THE INVENTION

The general terms used hereinbefore and hereinafter preferably have within the context of this disclosure the following meanings, unless otherwise indicated. Thus, the definitions of the general terms as used in the context of the present invention are provided herein below:

The singular forms "a," "an," and "the" include plural reference unless the context clearly dictated otherwise.

It will be understood that "substitution" or "substituted with" includes the implicit proviso that such substitution is in accordance with permitted valence of the substituted atom and the substituent, as well as represents a stable compound, which does not readily undergo transformation such as rearrangement, cyclization, elimination, etc.

The term "$C_1$-$C_4$alkyl" refers to the radical of saturated aliphatic groups, including straight or branched-chain containing from 1 to 4 carbon atoms. Examples of alkyl groups include but are not limited to methyl, ethyl, propyl, butyl, isopropyl, isobutyl, sec-butyl, tert-butyl and the like.

The term "$C_1$-$C_4$alkoxy" refers to an alkyl group as defined above attached via oxygen linkage to the rest of the molecule. Examples of alkoxy include, but are not limited to methoxy, ethoxy, propoxy, butoxy, tert-butoxy and the like.

The term "halogen" refers to fluorine, chlorine, bromine and iodine.

The term "hydroxy" or "hydroxyl" as used herein, refers to —OH group.

The term "therapeutically effective amount", as used herein refers to the amount of a compound represented by Formula (I), a pharmaceutically acceptable salt, a solvate, a stereoisomer or a diastereoisomer thereof, that, when administered to a subject in need of such treatment, is sufficient to inhibit the activity of human papillomavirus (HPV) such that the disease mediated by HPV is reduced, treated or alleviated.

The term "HPV" or "Human papillomavirus" as used herein refers to a member of the papillomavirus family of viruses that is capable of infecting mammals. The term includes both high-risk type and low risk type HPVs unless otherwise indicated.

The term "subject" as used herein, refers to an animal, preferably a mammal, most preferably a human, who is in the need of treatment of diseases mediated by HPV. The term subject may be interchangeably used with the term patient in the context of the present invention.

The term "mammal" as used herein is intended to encompass humans, as well as non-human mammals which are susceptible to infection by human papillomavirus. Non-human mammals include but are not limited to domestic animals, such as cows, pigs, horses, dogs, cats, rabbits, rats and mice, and non-domestic animals.

The term "treat" or "treatment" or "treated" with reference to HPV associated cancer in a subject, preferably a mammal, more preferably a human include: (i) inhibition of cancer i.e., arresting the development of the cancer; (ii) reduction in the regression of the cancer or slowing down of the cancer; (iii) amelioration of the cancer i.e., reducing the severity of the symptoms associated with the cancer (iv) relief, to some extent, of one or more symptoms associated with cancer.

As used herein the term "pharmaceutically acceptable" is meant that the carrier, diluent, excipients, and/or salt must be compatible with the other ingredients of the formulation, and not deleterious to the recipient thereof. "Pharmaceutically acceptable" also means that the compositions or dosage forms are within the scope of sound medical judgment, suitable for use for an animal or human without excessive toxicity, irritation, allergic response, or other problem or complication, commensurate with a reasonable benefit/risk ratio.

The present invention furthermore includes all solvates of the compounds of the formula (I), for example hydrates, and the solvates formed with other solvents of crystallization, such as alcohols, ethers, ethyl acetate, dioxane, dimethylformamide or a lower alkyl ketone, such as acetone, or mixtures thereof. Certain compounds of the present invention can exist in unsolvated forms as well as solvated forms, including hydrated forms. Certain compounds of the present invention may exist in multiple crystalline or amorphous forms. In general, all physical forms are equivalent for the uses contemplated by the present invention and are intended to be within the scope of the present invention.

The term "p53" refers to a nuclear phosphoprotein which acts as a tumor suppressor.

The term "pRb" or "retinoblastoma protein" refers to a tumor suppressor protein that is dysfunctional in many types of cancer.

The term "downregulation" refers to reducing, partially or totally, the indicated activity or expression. In the context of the present invention the term "downregulation of the oncoproteins E6 and E7" refers to the decrease in the expression level of E6 and E7 respectively. The level may be determined by any suitable method in the art, including Western blot assay.

The term "upregulation of p53" refers to increase in the expression level of the tumor suppressor protein 53.

The term "senescence" refers to the stage in which the cells lose their ability to divide.

The term "apoptosis" refers to the natural process of programmed cell death. It is a process of self-destruction, in which the cell uses specialized cellular machinery to kill itself. The cells disintegrate into membrane-bound particles that are then eliminated by phagocytosis. Apoptosis is a mechanism that enables metazoans to control cell number and eliminate cells that threaten the animal's survival.

The term "transcription" refers to a process of creating a complementary RNA copy of a sequence of DNA.

The term "cell cycle arrest" refers to a regulatory process that halts the progression through the cell cycle during one of the normal phases (G1, S, G2, M).

The compound with anti-cancer activity refers to a substance which is capable of inhibiting cell proliferation or is capable of inducing cell death. Non-limiting examples of anti-cancer agent suitable for use in the compositions of the invention include (i) microtubule disrupting agents such as taxanes and paclitaxel (ii) kinase inhibitors such as imatinib, erlotinib and BAY-43-9006, (iii) mTOR inhibitors such as rapamycin (iv) antineoplastic agents such as carboplatin, cisplatin, oxaliplatin, etoposide and Dacarbazine and (xvi) topoisomerase inhibitors such as topotecan and irinotecan (vi) antimetabolites such as cytarabine, fluorouracil, gemcitabine, topotecan, Hidroxyurea, Thioguanine, Methotrexate (vii) antibiotics such cytotoxic agents doxorubicin, bleomycin and dactinomycin.

According to one aspect of the present invention there is provided a compound of Formula (I), Formula (I)

wherein Ar is a phenyl group, which is unsubstituted or substituted by 1, 2, or 3 identical or different substituents selected from: halogen, nitro, cyano, $C_1$-$C_4$-alkyl, trifluoromethyl, hydroxyl or $C_1$-$C_4$-alkoxy; or a pharmaceutically acceptable salt, a solvate, a stereoisomer or a diastereoisomer thereof, for use in the treatment of a cancer associated with HPV.

According to one aspect of the invention there is provided a (+)-trans isomer of the compound of Formula (I), as indicated in Formula (IA) below, Formula (IA)

wherein Ar is a phenyl group, which is unsubstituted or substituted by 1, 2, or 3 identical or different substituents selected from halogen, nitro, cyano, $C_1$-$C_4$-alkyl, trifluoromethyl, hydroxyl or $C_1$-$C_4$-alkoxy; or a pharmaceutically acceptable salt thereof or a solvate thereof for use in the treatment of a cancer associated with HPV.

According to another aspect of the invention there is provided a compound of Formula (I), a pharmaceutically acceptable salt, a solvate, a stereoisomer or a diastereoisomer thereof, wherein Ar is phenyl group substituted by 1, 2, or 3 identical or different substituents selected from chlorine, bromine, fluorine, iodine, $C_1$-$C_4$-alkyl or trifluoromethyl, for use in the treatment of a cancer associated with HPV.

According to another aspect of the invention there is provided a compound of Formula (I), a pharmaceutically acceptable salt, a solvate, a stereoisomer or a diastereoisomer thereof, wherein Ar is phenyl group substituted by 1, 2, or 3 identical or different halogens selected from chlorine, bromine, fluorine or iodine, for use in the treatment of a cancer associated with HPV.

According to another aspect of the invention there is provided a compound of Formula (I), a pharmaceutically acceptable salt, a solvate, a stereoisomer or a diastereoisomer thereof, wherein Ar is phenyl group substituted by chlorine, for use in the treatment of a cancer associated with HPV.

According to another aspect of the invention there is provided a compound of Formula (I), a pharmaceutically acceptable salt, a solvate, a stereoisomer or a diastereoisomer thereof, wherein Ar is phenyl group substituted by chlorine and trifluromethyl, for use in the treatment of a cancer associated with HPV.

It will be appreciated by those skilled in the art that the compounds of Formula (I) contain at least two chiral centres and hence, exists in the form of two different optical isomers (i.e., (+) or (−) enantiomers), two different geometric isomers (cis and trans) and 4 different diasteroisomers. All such enantiomers, geometric isomers, diasteroisomers and mixtures thereof including racemic mixtures are included within the scope of the invention. The enantiomers of the compound of Formula (I) can be obtained by methods disclosed in PCT Application Publication Nos. WO2004004632, WO2007148158 and WO2008007169 incorporated herein by reference or the enantiomers of the compound of Formula (I) can also be obtained by methods well known in the art, such as chiral HPLC and enzymatic resolution. Alternatively, the enantiomers of the compounds of Formula (I) can be synthesized by using optically active starting materials.

The manufacture of the compounds of Formula (I), which may be in the form of pharmaceutically acceptable salts, and the manufacture of pharmaceutical composition suitable for oral, rectal and/or parenteral administration containing the above compounds are generally disclosed in PCT Application Publication No. WO2004004632, which is incorporated herein by reference.

As indicated herein above the compound of Formula (I) may be used in the form of their salts. Preferred salt of compounds of Formula (I) include acetates, alginates, ascorbates, aspartates, benzoates, benzenesulfonates, bisulfates, borates, cinnamates, citrates, ethanesulfonates, fumarates, glucuronates, glutamates, glycolates, hydrochlorides, hydrobromides, hydrofluorides, ketogjutarates, lactates, maleates, malonates, mesylate, nitrates, oxalates, palmoates, perchlorates, phosphates, picrates, salicylates, succinates, sulfamate, sulfates, tartrates, tosylate, trifluoroacetic acid salt and other acid addition salts known to the person skilled in the art.

Accordingly, an aspect of the invention, the compound of Formula (IA) for use in the treatment of HPV associated cancer is selected from (+)-trans-2-(2-Chloro-phenyl)-5,7-dihydroxy-8-(2-hydroxy-methyl-1-methyl-pyrrolidin-3-yl)-chromen-4-one hydrochloride (referred to herein as compound A) or (+)-trans-3-[2[(2-Chloro-4-trifluoromethyl-phenyl)-5,7-dihydroxy-8-(2-hydroxymethyl-1-methyl-pyrrolidin-3-yl)-chromen-4-one hydrochloride (referred to herein as compound B). Compounds A and B are disclosed in WO2007148158 and specifically as Example 10 and Example 44, respectively.

The compound of Formula (IA) for use in the treatment of HPV associated cancer can be (+)-trans-2-(2-Chloro-phenyl)-5,7-dihydroxy-8-(2-hydroxy-methyl-1-methyl-pyrrolidin-3-yl)-chromen-4-one hydrochloride (compound A).

The compound of Formula (IA) for use in the treatment of HPV associated cancer can be (+)-trans-3-[2[(2-Chloro-4-trifluoromethyl-phenyl)-5,7-dihydroxy-8-(2-hydroxymethyl-1-methyl-pyrrolidin-3-yl)-chromen-4-one hydrochloride (compound B).

The cancer associated with HPV is selected from the group consisting of anal cancer, vulvar cancer, vaginal cancer, penile cancer, cervical cancer, head and neck cancer such as oropharyngeal cancer and cancer of the oral cavity, lung cancer, non-melanoma skin cancer and cancer of the conjunctiva.

A compound of Formula (I), a pharmaceutically acceptable salt, a solvate, a stereoisomer or a diastereoisomer thereof can be used for the treatment of cervical cancer.

A method for the treatment of human papillomavirus associated cancer, comprising administering to the subject in need thereof a therapeutically effective amount of a compound of Formula (I) a pharmaceutically acceptable salt, a solvate, a stereoisomer or a diastereoisomer thereof is described.

HPV associated cancers selected from the group consisting of anal cancer, vulvar cancer, vaginal cancer, penile cancer, cervical cancer, head and neck cancer such as oropharyngeal cancer and cancer of the oral cavity, lung cancer, non-melanoma skin cancer and cancer of the conjunctiva in a subject, can be treated by administering to the subject in need thereof a therapeutically effective amount of a compound of Formula (I), a pharmaceutically acceptable salt, a solvate, a stereoisomer or a diastereoisomer thereof.

Cervical cancer can be treated by administering to the subject in need thereof a therapeutically effective amount of a compound of Formula (I), a pharmaceutically acceptable salt, a solvate, a stereoisomer or a diastereoisomer thereof.

The invention provides a method of inhibiting HPV associated cancer; comprising contacting the HPV infected cells with a compound of Formula (I).

According to an aspect of the invention there is provided a method of inhibiting high risk HPV selected from HPV 16, 18, 31, 33, 35, 39, 45, 51, 52, 56, 58, 59, 66 and 68, comprising contacting the HPV infected cells with a compound of Formula (I).

In an embodiment there is provided a method of inhibiting HPV 16, 18 and 31, comprising contacting the HPV infected cells with a compound of Formula (I).

According to this invention, the oncoproteins on HPV can be downregulated. The oncoproteins may be the oncoproteins E6 and E7 on HPV. The downregulation can be carried out by, administering to the subject a therapeutically effective amount of a compound of Formula (I). Inhibiting oncoproteins E6 and E7 on HPV is a means of inducing cell cycle arrest, senescence or apoptosis.

The oncoproteins E6 and E7 on HPV can be downregulated at transcriptional level.

The phosphoprotein p53 can be activated by administering a therapeutically effective amount of a compound of Formula (I) to the subject in need thereof.

According to yet another embodiment of the present invention there is provided a method of treatment of a cancer associated with HPV 16 comprising administering to the subject in need thereof a therapeutically effective amount of a compound of Formula (I), a pharmaceutically acceptable salt, a solvate, a stereoisomer or a diastereoisomer thereof.

According to another aspect of the invention, there is provided a method for the manufacture of medicaments, comprising a compound of Formula (I), a pharmaceutically acceptable salt, a solvate, a stereoisomer or a diastereoisomer thereof which are useful for the treatment of a cancer associated with HPV.

There is provided a pharmaceutical composition which comprises a therapeutically effective amount of compound of Formula (I), a pharmaceutically acceptable salt, a solvate, a stereoisomer, or a diastereoisomer thereof in association with a pharmaceutically acceptable carrier. The composition can include at least one further pharmaceutically active compound, wherein the further pharmaceutically active compound has anticancer activity. The pharmaceutically active compound can be selected from, but not limited to, bleomycin, cispaltin, topotecan hydrochloride, imiquimod, podofilox, trichloroacetic acid and the like.

The pharmaceutical preparations may contain about 1 to 99%, for example, about 5 to 70%, or from about 5 to about 30% by weight of the compound of the Formula (I) or pharmaceutically acceptable salt thereof. The amount of the active ingredient of the Formula (I) or pharmaceutically acceptable salt thereof in the pharmaceutical preparations normally is from about 1 to 1000 mg.

The compound of Formula (I) may be administered orally, intravaginally, vulvovaginally, rectally, topically or parenterally (including intravenous, subcutaneous, intramuscular, intravascular or infusion). The compound of Formula (I) may have to be administered by any route appropriate to the condition to be treated. It will be appreciated that the preferred route may vary with the condition of the patient.

Compositions intended for pharmaceutical use may be prepared according to any method known in the art for the manufacture of pharmaceutical compositions, e.g. *Remington—The Science and Practice of Pharmacy* ($21^{st}$ *Edition*) (2005), *Goodman & Gilman's The Pharmacological Basis of Therapeutics* ($11^{th}$ *Edition*) (2006) and *Ansel's Pharmaceutical Dosage Forms and Drug Delivery Systems* ($9^{th}$ *Edition*), edited by Allen et al., Lippincott Williams & Wilkins, (2011), *Solid-State Chemistry of Drugs* ($2^{nd}$ *Edition*)(1999), each of which is hereby incorporated by reference."

The compositions described herein may be in a form suitable for oral administration, for example as a tablet or capsule; for parenteral injection (including intravenous, subcutaneous, intramuscular, intravascular or infusion) for example as a sterile solution, suspension or emulsion; for topical administration for example as an ointment, cream, gel, lotions or collodion; for rectal, vaginal or vulvovaginal administration for example as a suppository, tampons, pessaries, creams, gels, paste, foam or vaginal ring. The composition can be administered topically to external surfaces of skin surface, such as vulva and/or to surrounding areas of skin. In addition or alternatively, the composition can be administered intravaginally.

For oral use, the compound of Formula (I) may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc and sugar.

For intramuscular, intraperitoneal, subcutaneous and intravenous use, sterile solutions of compound of Formula (I) are usually employed, and the pH of the solutions should be suitably adjusted and buffered.

For ointments, creams, the compound of Formula (I) is formulated in oil-in-water or water-in-oil base. A vaginal cream can be administered to contact a mucosal surface in the vaginal cavity.

For rectal or vaginal use, the compound of Formula (I) can be administered in the form of suppositories. A suppository comprises of compound of Formula (I), a suitable suppository base and additives such as preservatives, antioxidants, emulsifiers and the like. Suitable suppository bases include natural or synthetic triglycerides or paraffin hydrocarbons. The vaginal use the compound of Formula (I) can also be administered in the form of vaginal cream.

Compositions for oral delivery may be in the form of tablets, lozenges, aqueous or oily suspensions, granules, powders, emulsions, capsules, syrups, or elixirs. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Selectively permeable membranes surrounding an osmotically active driving compound are also suitable for oral administration of compounds of present invention. Oral compositions can include standard vehicles such as mannitol, lactose, starch, magnesium stearate, sodium saccharine, cellulose, magnesium carbonate, etc. Such vehicles are preferably of pharmaceutical grade.

Further, the effect of the compounds of the present invention contained in the pharmaceutical composition may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

Compositions for rectal administration or vaginal administration are suppositories. Suppositories are solid bodies for insertion into the rectum or vagina which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Suppositories may be prepared either by the compressed method or by molding.

Effective dose of the compound of Formula (I) depends at least on the nature of the condition being treated, the mode of delivery, and the pharmaceutical formulation, and will be determined by the clinician using conventional dose escalation studies. It can be expected to be from about 0.1 to about 100 mg/kg body weight per day; particularly, from about 0.1 to about 10 mg/kg body weight per day; more particularly, from about 0.1 to about 5 mg/kg body weight per day.

Compounds of Formula (I) may be prepared according to the methods disclosed in PCT Patent Publication No. WO2004004632 and PCT Patent Publication No. WO2007148158 which are incorporated herein by reference.

The general process for the preparation of compounds of Formula (I), or a pharmaceutically acceptable salt thereof, comprises the following steps:

(a) treating the resolved enantiomerically pure (−)-trans enantiomer of the intermediate compound of Formula VIA, with acetic anhydride in the presence of a Lewis acid catalyst to obtain a resolved acetylated compound of Formula VIIA, (b) reacting the resolved acetylated compound of Formula VIIA with an acid of Formula ArCOOH or an acid chloride of Formula ArCOCl or an acid anhydride of Formula (ArCO)$_2$O or an ester of Formula ArCOOCH$_3$, wherein Ar is as defined hereinabove in reference to the compound of Formula (I), in the presence of a base and a solvent to obtain a resolved compound of Formula VIIIA;

(c) treating the resolved compound of Formula VIIIA with a base in a suitable solvent to obtain the corresponding resolved β-diketone compound of Formula IXA;

IXA wherein Ar is as defined above;
(d) treating the resolved β-diketone compound of Formula IXA with an acid such as hydrochloric acid to obtain the corresponding cyclized compound of Formula XA,

XA (e) subjecting the compound of Formula XA to dealkylation by heating it with a dealkylating agent at a temperature ranging from 120-180° C. to obtain the (+)-trans enantiomer of the compound of Formula (I) and, optionally, converting the subject compound into its pharmaceutically acceptable salt.

The Lewis acid catalyst utilized in the step (a) above may be selected from: $BF_3$, $Et_2O$, zinc chloride, aluminium chloride and titanium chloride.

The base utilized in the process step (b) may be selected from triethylamine, pyridine and a DCC-DMAP combination (combination of N, N'-dicyclohexyl carbodiimide and 4-dimethylaminopyridine).

It will be apparent to those skilled in the art that the rearrangement of the compound of Formula VIIIA to the corresponding β-diketone compound of Formula IXA is known as a Baker-Venkataraman rearrangement (J. Chem. Soc., 1933, 1381 and Curr. Sci., 1933, 4, 214).

The base used in the process step (c) may be selected from: lithium hexamethyl disilazide, sodium hexamethyldisilazide, potassium hexamethyldisilazide, sodium hydride and potassium hydride. A preferred base is lithium hexamethyl disilazide.

The dealkylating agent used in process step (e) for the dealkylation of the compound of Formula IXA may be selected from: pyridine hydrochloride, boron tribromide, boron trifluoride etherate and aluminium trichloride. A preferred dealkylating agent is pyridine hydrochloride.

Preparation of the starting compound of Formula VIA involves reacting 1-methyl-4-piperidone with a solution of 1,3,5-trimethoxybenzene in glacial acetic acid, to yield 1-methyl-4-(2,4,6-trimethoxyphenyl)-1,2,3,6-tetrahydropyridine, which is reacted with boron trifluoride diethyl etherate, sodium borohydride and tetrahydrofuran to yield 1-methyl-4-(2,4,6-trimethoxyphenyl)piperidin-3-ol. Conversion of 1-methyl-4-(2,4,6-trimethoxyphenyl)piperidin-3-ol to the compound of Formula VIA involves converting the hydroxyl group present on the piperidine ring of the compound, 1-methyl-4-(2,4,6-trimethoxyphenyl) piperidin-3-ol to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol.

It is to be understood that the invention may assume various alternative variations and step sequences, except where expressly specified to the contrary.

Moreover, other than in any operating examples, or where otherwise indicated, all numbers expressing, for example, quantities of ingredients used in the specification and claims are to be understood as being modified in all instances by the term "about".

Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Those skilled in the art will recognize that several variations are possible within the scope and spirit of this invention. The invention will now be described in greater detail by reference to the following non-limiting examples. The following examples further illustrate the invention but, of course, should not be construed as in any way limiting its scope.

EXEMPLIFICATION

In the following examples and elsewhere, abbreviations have the following meanings:

| List of abbreviations | |
|---|---|
| ATCC | American Type Cell Culture |
| bp | Base pairs |
| $BF_3$ | boron trifluoride |
| $CO_2$ | carbon dioxide |
| cDNA | complementary DNA |
| DMEM | Dulbecco's Modified Eagle Medium |
| DMSO | dimethyl sulfoxide |
| DNA | deoxyribonucleic acid |
| dsDNA | double stranded Deoxyribonucleic Acid |
| dNTPs | Deoxynucleotide Triphosphates |
| e.e | enantiomeric excess |
| EGFP | enhanced green fluorescent protein |
| $Et_2O$ | diethyl ether |
| FBS | fetal bovine serum |
| g | Gram |
| H | hour(s) |
| HCl | hydrochloric acid |
| HPLC | high performance liquid chromatography |
| HRP | horseradish peroxidase |
| ip | intraperitoneally |

List of abbreviations

| | |
|---|---|
| IPA | isopropyl alcohol |
| MeOH | Methanol |
| μg | Microgram |
| μL | microlitre |
| mg | milligram |
| mL | milliliter |
| mm | millimetre |
| mmol or mM | millimolar |
| mpk | milligram per kilogram |
| $MgCl_2$ | magnesium Chloride |
| MMLV-RT | Moloney Murine Leukemia virus Reverse Transcriptase |
| $Na_2CO_3$ | sodium carbonate |
| ng | nanogram |
| NP-40 | nonyl phenoxypolyethoxylethanol |
| NaF | sodium fluoride |
| $Na_3VO_4$ | sodium orthovanadate |
| NaCl | sodium chloride |
| nm | Nanometers |
| pmol | Picomolar |
| PCR | polymerase chain reaction |
| p.o | per oral |
| RNA | ribonucleic Acid |
| RT-PCR | Reverse transcription polymerase chain reaction |
| SDS-PAGE | sodium dodecyl sulfate polyacrylamide gel electrophoresis |
| TFA | trifluoroacetic acid |
| UV | Ultraviolet |

Example 1

A) Preparation of (+)-trans-2-(2-Chlorophenyl)-5,7-dihydroxy-8-(2-hydroxymethyl-1-methyl-pyrrolidin-3-yl)-chromen-4-one hydrochloride (Compound A)

Molten pyridine hydrochloride (4.1 g, 35.6 mmol) was added to (+)-trans-2-(2-chloro-phenyl)-8-(2-hydroxymethyl-1-methyl-pyrrolidin-3-yl)-5,7-dimethoxy-chromen-4-one (0.4 g, 0.9 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (5 mL), stirred for 30 minutes filtered and dried to obtain the compound, (+)-trans-2-(2-chloro-phenyl)-5,7-dihydroxy-8-(2-hydroxymethyl-1-methyl-pyrrolidin-3-yl)-chromen-4-one.

Yield: 0.25 g (70%);
IR (KBr): 3422, 3135, 1664, 1623, 1559 $cm^{-1}$;
1H NMR ($CDCl_3$, 300 MHz): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H); MS (ES+): m/z 402 (M+1);
Analysis: $C_{21}H_{20}ClNO_5$; C, 62.24 (62.71); H, 5.07 (4.97); N, 3.60 (3.48); Cl, 9.01 (8.83).

The compound (0.2 g, 0.48 mmol) as obtained above was suspended in IPA (5 mL) and 3.5% HCl (25 mL) was added. The suspension was heated to get a clear solution. The solution was cooled and filtered to obtain the compound, (+)-trans-2-(2-Chlorophenyl)-5,7-dihydroxy-8-(2-hydroxymethyl-1-methyl-pyrrolidin-3-yl)chromen-4-one hydrochloride.

Yield: 0.21 g (97%); mp: 188-192° C.; [α] D25=+21.3° (c=0.2, methanol);
1H NMR ($CD_3OD$, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H); MS (ES+): m/z 402 (M+1)(free base).

This compound was subjected to chiral HPLC. Chiral HPLC was done using column Chiralcel OD-H (250×4.6 mm) and solvent system haxane:ethanol (92:08) with TFA (0.4%). The results are recorded at 264 nm with solvent flow rate of 1 mL/minute The chiral HPLC showed 100% e.e of the compound, (+)-trans-2-(2-chloro-phenyl)-5,7-dihydroxy-8-(2-hydroxy-methyl-1-methyl-pyrrolidin-3-yl)-chromen-4-one hydrochloride.

B) Preparation of (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride (Compound B)

A mixture of the compound, (+)-trans-2-(2-Chloro-4-trifluoromethylphenyl)-8-(2-hydroxymethyl-1-methyl pyrrolidin-3-yl)-5,7-dimethoxy-chromen-4-one (0.25 g, 0.5 mmol), pyridine hydrochloride (0.25 g, 2.16 mmol) and a catalytic amount of quinoline was heated at 180° C. for a period of 2.5 h. The reaction mixture was diluted with methanol (25 mL) and basified with solid $Na_2CO_3$ to pH 10. The reaction mixture was filtered, and washed with methanol. The organic layer was concentrated and the residue purified by column chromatography using 0.1% ammonia and 4.5% MeOH in chloroform as eluent to yield the compound, (+)-trans-2-(2-chloro-4-trifluoromethylphenyl)-5,7-dihydroxy-8-(2-hydroxy-methyl-1-methylpyrrolidin-3-yl)-chromen-4-one, as a yellow solid.

Yield: 0.15 g (63.7%);
$^1$H NMR ($CDCl_3$, 300 MHz): δ 7.99 (m, 2H), 7.83 (d, 1H), 6.65 (s, 1H), 6.41 (s, 1H), 4.24 (m, 1H), 3.90 (m, 2H), 3.70 (m, 1H), 3.60 (m, 1H), 3.41 (m, 1H), 2.99 (s, 3H), 2.54 (m, 1H), 2.28 (m, 1H); MS (ES+): m/z 470 (M+1).

The compound (0.1 g, 0.2 mmol) as obtained above was suspended in methanol (2 mL) and treated with ethereal HCl and the organic solvent evaporated to yield the compound, (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride.

Yield: 0.1 g (92.8%);
1H NMR ($CDCl_3$, 300 MHz): δ 8.02 (d, 2H), 7.83 (d, 1H), 6.64 (s, 1H), 6.41 (s, 1H), 4.23 (m, 1H), 3.73 (m, 2H), 3.68 (m, 1H), 3.51 (m, 1H), 3.39 (m, 1H), 2.99 (s, 3H), 2.54 (m, 1H), 2.31 (m, 1H).

In Vitro Studies

Materials and Methods: Two cervical cancer cell lines SiHa and HeLa (ATCC), positive for HPV genome were used for evaluation of Compound A and Compound B. The cell lines were transfected with a plasmid vector expressing p53 protein fused with a fluorescent protein EGFP using lipofectamine (Invitrogen, CA, USA). After 48 h of transfection the cells were maintained for 30-45 days in DMEM (Sigma Aldrich, catalogue no. D5546) supplemented with 10% FBS and 800 μg/mL Geneticin (Gibco BRL Life Technologies, Inc) for 30-45 days. The stably expressing cells were expanded and evaluated for the presence of fusion construct under fluorescent microscopy. After 24 h of transfection, the cells were treated separately with Compound A and Compound B (henceforth referred to as treated cells) for 24 h. Cells were harvested and were used for analysis of status of E6, E7, p53 by western blot and by RT-PCR. Cells not treated with the Compound A and Compound B (henceforth referred to as untreated cells) were used as controls. HPV negative C33A cell was used as negative control.

The terms fresh medium and culture medium refer to DMEM (catalogue no. D5546).

Example 2: Analysis of Status of E6, E7, p53 by Western Blot

To prepare whole cell extracts for Western blot, the treated cells were lysed in lysis buffer (50 mM Tris-HCl (pH 7.4), 1% NP-40, 40 mM NaF, 10 mM NaCl, 10 mM $Na_3VO_4$, 1 mM phenylmethylsulfonyl fluoride, and 10 mM dithiothreitol and 1 μg/ml each of leupeptin and aprotinin). The cell lysates (50 μg) were resolved by SDS-PAGE and the separated proteins (E6, E7 and p53) were transferred to polyvinylidene difluoride membrane (PVDF) by wet transfer method using Bio-Rad electro-transfer apparatus. After blocking with 10% non-fat milk in Tris buffered saline containing 0.2% Tween-20, the membrane was incubated with the primary antibody, followed by HRP-conjugated secondary antibody. Proteins were visualized by 3, 3'-Di amino benzidine (DAB) method. Similar procedure was followed for untreated cells.

The following antibodies were used for western blot with the indicated dilutions.

Primary Antibodies

| Sr. No. | Antibody | Source Organism | Company | Dilution |
|---|---|---|---|---|
| 1 | p53 Antibody | Rabbit | Cell Signaling (9282) | 1:500 |
| 2 | HPV16 E7(NM2) | Mouse | SantaCruz (sc-65711) | 1:100 |
| 3 | HPV E76 (N-17) | Goat | SantaCruz (sc-1584) | 1:100 |
| 4 | Beta actin | Mouse | Sigma (A5316) | 1:1000 |

Secondary Antibodies

| Sr. No. | Antibody | Company | Dilution |
|---|---|---|---|
| 1 | Rabbit anti goat HRP | Molecular Probes (R21459) | 1:2000 |
| 2 | Anti mouse HRP | Sigma (A9044) | 1:2000 and 1:4000 |
| 3 | Anti rabbit HRP | Sigma (A0545) | 1:2000 |

Figure 1A:
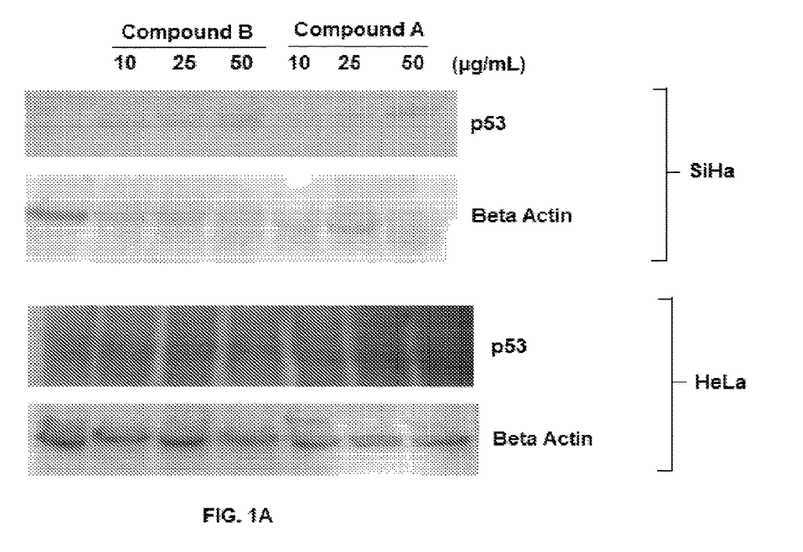
FIG. 1A depicts the reproductions of Western blots showing significant upregulation of p53 in the cells treated with compound A and compound B.
Figure 1B:
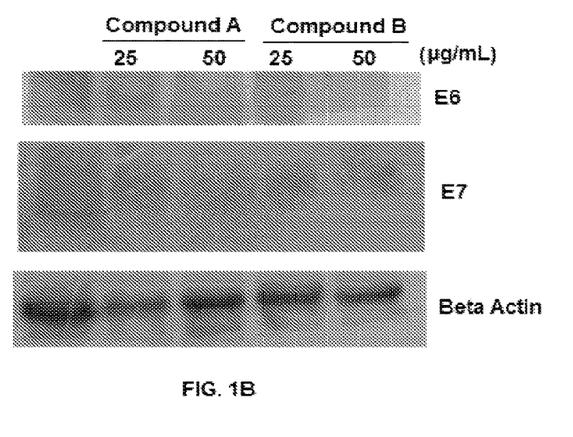
FIG. 1B depicts the reproductions of Western blots showing significant downregulation of expression of E6 and E7 in SiHa cells treated with compound A and compound B.

Results: It was observed that cells treated with Compound A and Compound B showed increased expression of p53 protein in a dose dependant manner in both SiHa and HeLa cells. However no expression was observed in untreated cells. The expression of E6 was down regulated in SiHa cells by both the compounds at the concentration of 50 μg/mL. Similarly the complete down regulation of E7 was seen in cells treated with 25 μg/mL of Compound A and also complete down regulation of E7 was seen in cells treated with 25 μg/mL of Compound B compared to control (FIG. 1A and FIG. 1B).

Example 3: Analysis of Status of E6, E7, p53 by RT-PCR

The expression status for gene E6 and E7 at the transcription level was detected by Reverse Transcriptase PCR (RT-PCR). The RNA was isolated from the treated and untreated cells using Qiagen AllPrep DNA/RNA Mini Kit (Cat. No. 80204). The RNA integrity was checked by visualization under UV after agarose gel electrophoresis. The quantity and purity of RNA was analysed by Nano Drop (Thermo Scientific). The 500 ng of RNA was converted into cDNA using 0.1 μg/μl of Oligo dT (Promega), MMLV-RT, dNTPs, RNA guard and RT buffer (Promega) and incubated at 37° C. for 1 h. The reaction was terminated by heating the reaction mixture at 90° C. for 3 minutes and used for PCR amplification of E6 and E7 genes. The PCR was conducted as follows:

| | | | |
|---|---|---|---|
| 5x Buffer | 3 μl | 10 mM dNTPs | 0.8 μl |
| DNA taq polymerase | 0.3 μl | Sense primer (10 pmol) | 1 μl |
| Antisense primer (10 pmol) | 1 μl | $MgCl_2$ (50 mM) | 0.45 μl |
| Sterile water | 5.45 μl | cDNA | 3 μl |

The sequence of the primers are shown below

| Gene | Primer Sequence | Size |
|---|---|---|
| β-Actin sense | 5'-AGACTTCGAGCAGGAGATG-3' (SEQ ID NO: 1) | 256 bp |
| Antisense | 5'-CTTGATCTTCATGGTGCTAGG-3' (SEQ ID NO: 2) | |
| 16 E6 sense | 5'-TGAGGTATATGACTTTGCTTTTC-3' (SEQ ID NO: 3) | 297 bp |
| Antisense | 5'-CAAGACATACATCGACCGGTCC-3' (SEQ ID NO: 4) | |
| 16 E7 sense | 5'-AAATGACAGCTCAGAGGAGGAG-3' (SEQ ID NO: 5) | 209 bp |
| Antisense | 5'GTTTCTGAGAACAGATGGGGCAC-3' (SEQ ID NO: 6) | |

Figure 2:
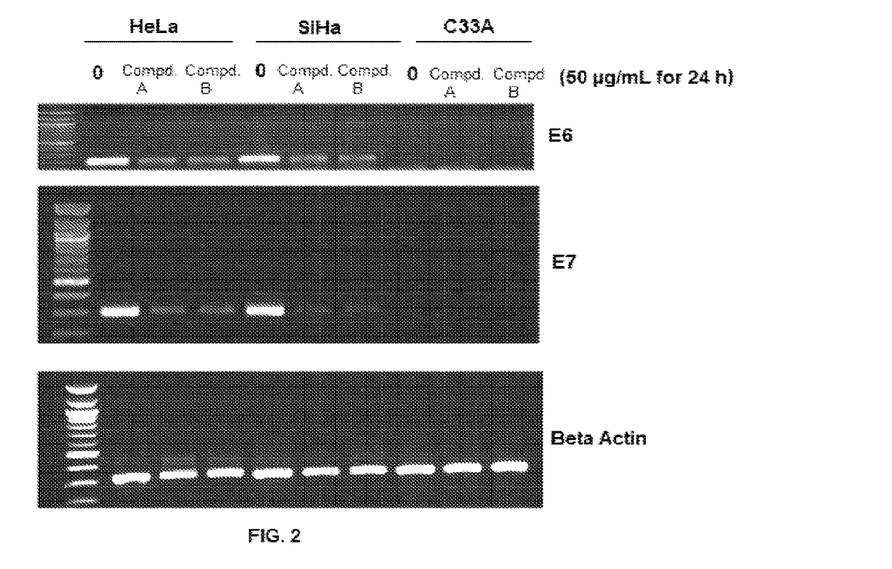
FIG. 2 depicts the reproductions of RT-PCR showing significant downregulation of expression of E6 and E7 in SiHa and HeLa cells treated with compound A and compound B at the transcription level.

Results: RT-PCR quantification revealed significant inhibition of transcripts for both E6 and E7 in both SiHa and HeLa cells treated with 50 μg/mL of either Compound A or Compound B. The β-actin was used as a house keeping gene to normalize the data in RT-PCR assay. The specificity of gene specific PCR was determined using C33A cells which are negative for E6 and E7 genes (FIG. 2).

Example 4: p53 Nuclear Translocation Assay

Materials and methods: Two cervical cancer cell lines SiHa and HeLa (ATCC), positive for HPV genome were used. The cell lines were transfected with the expression vector containing p53-EGFP using lipofectamine (Invitrogen, CA, USA). After 48 h of transfection the cells were maintained for 30-45 days in DMEM (Sigma Aldrich, catalogue no. D5546) supplemented with 10% FBS and 800 μg/mL Geneticin (Gibco BRL Life Technologies, Inc) for 30-45 days. The stably expressing cells were used for the p53 Nuclear Translocation Assay.

Biological Studies: The stably expressing cells were seeded on 96 well imaging plates (Becton Dickinson, USA) and allowed to grow for 48 h in a humidified $CO_2$ incubator at 37° C. The cell nucleus were stained with vital fluorescent nuclear dye Hoechst 22334 (0.5 μg/mL) for 5 minutes followed by fresh medium replacement. A stock solution of 50 mg/mL was prepared in DMSO and further dilutions were made to obtain the concentration of 2-50 μg/mL were made in the culture medium containing 5% FBS. Cells were treated separately with different concentrations (2-50 μg/mL) of Compound A and Compound B. The imaging was carried out at every 12 h using pathway Bio imager (BD, USA) using 20× objective. The cells were segmented based on the nuclear channel and number of cells positive for nuclear—EGFP were calculated to score activity. Alternatively the cells were also imaged with Nikon Ti inverted fluorescent microscope equipped with CCD camera Retiga Exi and NIS element software. The bright field images were also collected.

Figure 3A:
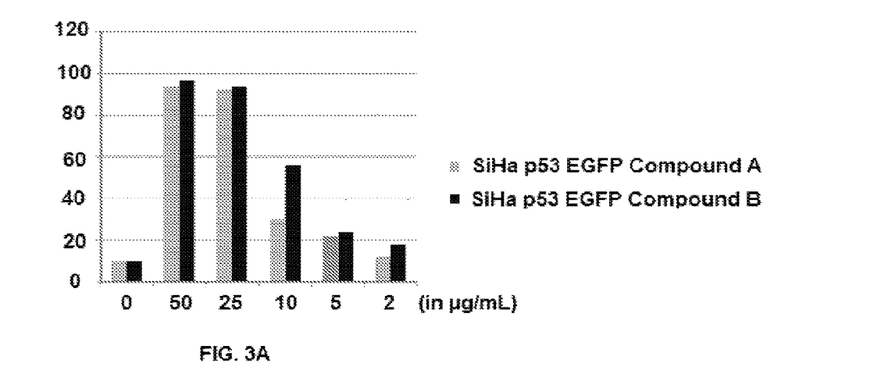
FIG. 3A is a graphical representation of p53-EGFP nuclear translocation in SiHa cells.
Figure 3B:
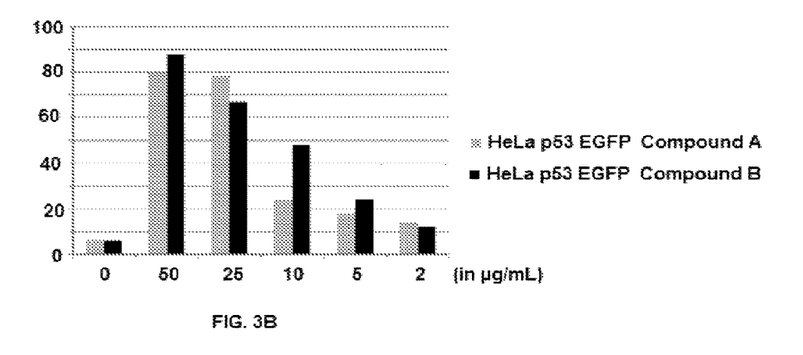

Results: Microscopic imaging for nuclear translocation of EGFP linked p53 protein demonstrated that addition of Compound A and Compound B resulted in increased nuclear translocation of EGFP-p53 protein in both HeLa and SiHa cells. Further it was also noticed that nuclear translocation was initiated at 12 h post treatment and increased up to 24 h at 25 and 50 kg/mL concentration of Compound A as well as Compound B. The representative graph showing the percentage p53 EGFP nuclear positive cell for each drug for the different concentration of drug is shown in (FIG. 3A and FIG. 3B).

Example 5: Senescence Assay

This assay was performed to detect senescence associated β-galactosidase staining to check the senescence status in the treated cells.

Materials and methods: Two cervical cancer cell lines SiHa and HeLa (ATCC), positive for HPV genome were used. The cell lines were transfected with the expression vector containing p53-EGFP using lipofectamine (Invitrogen, CA, USA). After 48 h of transfection the cells were maintained for 30-45 days in DMEM (Sigma Aldrich, catalogue no. D5546) supplemented with 10% FBS and 800 μg/mL Geneticin (Gibco BRL Life Technologies, Inc) for 30-45 days. The stably expressing cells were used for the Senescence assay.

Biological Studies: The stably expressing cells were treated with Compound A and Compound B separately and fixed for 5 minutes in 3% formaldehyde, washed, and incubated at 37° C. with 5-bromo-4-chloro-3-indolyl δ-D-galactopyranoside solution (1 mg/ml), (prepared by dissolving in a solution containing 40 mM citric acid (pH 6.5), 5 mM potassium ferrocyanide, 5 mM potassium ferricyanide, 150 mM NaCl, and 2 mM $MgCl_2$). After overnight incubation at 37° C., tissues or cells were visualized by microscopy. The intense blue staining in the cytosol indicated the induction of senescent like features in the cells.

Example 6: In Vivo Assay

All experiments were carried out in accordance with the guidelines of Committee for the Purpose of Control and Supervision of Experiments on Animals (CPCSEA) and with the approval of Institutional Animal Ethics Committee (IAEC) in Piramal Healthcare Limited, Goregoan, Mumbai, India.

In vivo efficacy of the compounds of the present invention for the treatment of HPV associated cancer was studied by using SiHa (HPV 16 positive cervical cancer) cell line.

SiHa Human Cervical Cancer Xenograft Mouse Model

Animals used: Nude Nu/J, Homozygous for FOXn1(Nu) male mice, 4 to 6 weeks old, weighing 22 to 25 g (Harlan Laboratories, US). Animals were housed in animal isolator under specified pathogen-free conditions maintained at 22 to 25° C. and 55 to 75% humidity, with a 12-hour light/12-hour dark cycle. The mice were acclimatized for a period of seven days before experimentation. Animals were handled in a laminar flow hood. All food and water was autoclaved.

Generation of Subcutaneous Xenograft Tumors in Nude Mice

Step 1: Preparation of a Single-Cell Suspension for Injection into Nude Mice

The adherent SiHa cells (SiHa cell line—ATCC—HBT 35) were harvested using Trypsin-EDTA solution and suspension was centrifuged at 800 rpm for 5 minutes. The supernatant was removed and the cell pellet was re-suspended in 1 mL serum-free MEM medium. The cell count was obtained using 1:100 dilution. The cells were diluted to obtain $5 \times 10^6$ cells per 0.2 mL of suspension.

Step 2: Generation of Subcutaneous Xenograft Tumors in Nude Mice

On the day of tumor cell injection, cell suspension of step 1 was stored on ice in the laminar airflow hood. Each nude mouse was injected with 0.2 mL of the cell suspension subcutaneously on the right flank. The animals were observed after 5 days for tumor growth by palpation around the injection site.

Conditions for Storage of the Compounds and Dose Preparation

Compound A: 3.5 mg/mL; vehicle: dextrose (5%) prepared in water.

Topotecan Hydrochloride (used as standard): 0.2 mg/mL; vehicle: methyl cellulose (0.25%).

Compound B: 20 mg/mL; vehicle: methyl cellulose (0.25%).

Cisplatin (used as standard): 0.6 mg/mL; vehicle: methyl cellulose (0.25%).

All the compounds including the standard were stored at 4° C. to 8° C.

Dosing

Nude mice were housed in a group of 8 per cage (filter-top cages) with autoclaved husk bedding and free access to food and water was provided. Animals were handled as per the standard guidelines. Treatment was initiated when tumor size volume was about 100 $mm^3$. The tumor-bearing mice were randomized (n=8) in the following groups of treatment:
  i) Group 1: Control group: Tumor-bearing mice administered with vehicle.
  ii) Group 2: Tumor-bearing mice administered once daily with 35 mg/kg of compound A intraperitoneally.
  iii) Group 3: Tumor-bearing mice were administered with a single dose of 2 mg/kg of Topotecan (standard) intraperitoneally.
  iv) Group 4: Tumor-bearing mice were administered once daily with 200 mg/kg of Compound B p.o.
  v) Group 5: Tumor-bearing mice were administered with a single dose of 6 mg/kg of Cisplatin (standard) intraperitoneally.

Treatment

Nude mice of Group 1, Group 2 and Group 4 were treated on days 1-6 and 12-17. Group 3 and Group 5 mice were treated on day 1. On the 23$^{rd}$ day animals from all groups were scarified and samples were harvested for further analysis.

The volume administered to all the above Groups was 10 mL/kg.

Observations and Measurement

Following parameters were observed during treatment:
1. Gross animal health was observed everyday
2. Body weight was observed everyday
3. Tumor was measured 2-3 days apart, using vernier caliper. Tumor volume in mm³ was calculated using the formula for a prolate ellipsoid:

Tumor volume (mm³)=Length (mm)×[Breadth (mm)²]×0.5 assuming specific gravity of tumor as 1 and π as 3
Treated to control ratio (ΔT/ΔC %) on a given day was calculated using the formula:

$$\Delta T/\Delta C \% \text{ on Day } X = \frac{\text{Tumor size Compound}_{Day\,X} - \text{Tumor size Compound}_{Day\,0}}{\text{Tumor size control}_{Day\,X} - \text{Tumor size control}_{Day\,0}} \times 100$$

Figure 4:
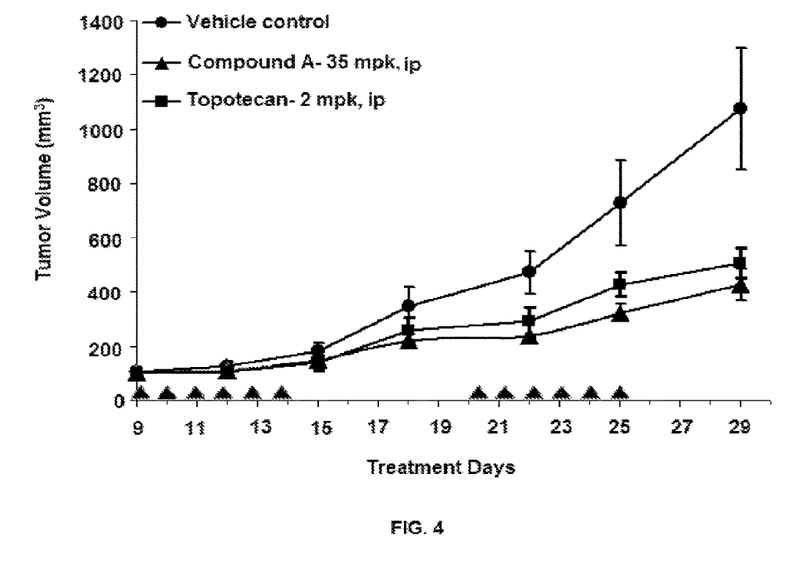
FIG. 4 is a graphical representation of tumor growth profile in SiHa xenograft animals after administration of Compound A.
Figure 5:
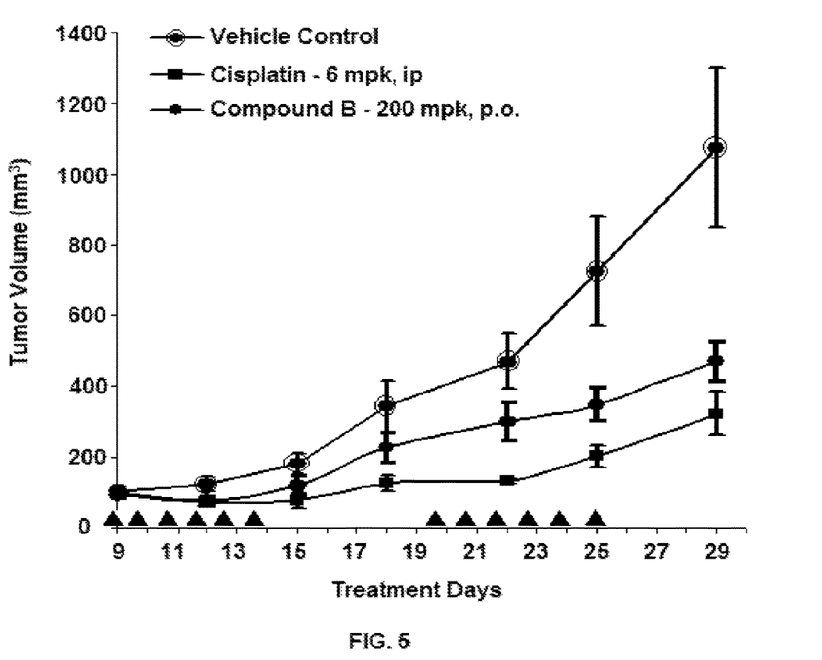
FIG. 5 is a graphical representation of tumor growth profile in SiHa xenograft animals after administration of Compound B.

Growth inhibition (GI) was calculated using the formula $GI$ on Day $X = 100 - \Delta T/\Delta C \%$ on Day $X$ Tumor growth inhibition results are given in FIG. 4 and FIG. 5.

CONCLUSION

Compound A and Compound B showed significant tumor growth inhibition in HPV mediated cervical cancer xenograft model.

---

We claim:

1. A method of treating human papillomavirus (HPV) associated cancer comprising administering to a subject in need thereof a therapeutically effective amount of a compound of Formula (I), or a pharmaceutically acceptable salt or solvate thereof;

formula (I)

wherein Ar is 2-chloro-4-trifluoromethylphenyl, and the HPV associated cancer is selected from anal cancer, vulvar cancer, vaginal cancer, penile cancer, cervical cancer, non-melanoma skin cancer, and cancer of the conjunctiva.

2. The method of claim 1, wherein the compound of Formula (I) is a (+)-trans isomer represented by Formula (IA), or a pharmaceutically acceptable salt or a solvate thereof;

formula (IA)

wherein Ar is 2-chloro-4-trifluoromethylphenyl.

3. The method of claim 2, wherein the compound of Formula (IA) is (+)-trans-2-(2-Chloro-4-trifluoromethyl-phenyl)-5,7-dihydroxy-8-(2-hydroxymethyl-1-methylpyrrolidin-3-yl)-chromen-4-one hydrochloride.

4. The method of claim 1, wherein the HPV associated cancer is cervical cancer.

5. The method of claim 1, wherein the compound of Formula (I) or a pharmaceutically acceptable salt or solvate thereof, is formulated in a pharmaceutical composition further comprising a pharmaceutically acceptable carrier.

6. The method of claim 1, wherein the HPV associated cancer is anal cancer.

7. The method of claim 1, wherein the HPV associated cancer is vulvar cancer.

8. The method of claim 1, wherein the HPV associated cancer is vaginal cancer.

9. The method of claim 1, wherein the HPV associated cancer is penile cancer.

10. The method of claim 1, wherein the HPV associated cancer is non-melanoma skin cancer.

11. The method of claim 1, wherein the HPV associated cancer is cancer of the conjunctiva.

* * * * *